(12) United States Patent
Holsti et al.

(10) Patent No.: US 10,583,267 B2
(45) Date of Patent: Mar. 10, 2020

(54) APPARATUS AND METHODS FOR IMPROVING HEALTH OUTCOMES OF PRETERM INFANTS

(71) Applicant: BRITISH COLUMBIA CANCER AGENCY BRANCH, Vancouver (CA)

(72) Inventors: Liisa Holsti, Vancouver (CA); Karon MacLean, Vancouver (CA); Henry Voss, West Vancouver (CA)

(73) Assignee: British Columbia Cancer Agency Branch, Vancouver (CA)

( * ) Notice: Subject to any disclaimer, the term of this patent is extended or adjusted under 35 U.S.C. 154(b) by 315 days.

(21) Appl. No.: 15/516,287

(22) PCT Filed: Oct. 2, 2015

(86) PCT No.: PCT/CA2015/051002
§ 371 (c)(1),
(2) Date: Mar. 31, 2017

(87) PCT Pub. No.: WO2016/049780
PCT Pub. Date: Apr. 7, 2016

(65) Prior Publication Data
US 2017/0252532 A1    Sep. 7, 2017

Related U.S. Application Data

(60) Provisional application No. 62/203,071, filed on Aug. 10, 2015, provisional application No. 62/059,274, filed on Oct. 3, 2014.

(51) Int. Cl.
*A61M 21/02* (2006.01)
*A61G 11/00* (2006.01)
(Continued)

(52) U.S. Cl.
CPC .......... *A61M 21/02* (2013.01); *A61G 11/002* (2013.01); *A61G 11/008* (2013.01);
(Continued)

(58) Field of Classification Search
CPC .............. A61M 21/0094; A61M 21/02; A61M 2021/0027; A61M 2021/0022;
(Continued)

(56) References Cited

U.S. PATENT DOCUMENTS 2,897,518 A    12/1958   Paramore
3,158,150 A *  11/1964   Croasdaile ............. A61G 11/00
                                                              600/22
(Continued)

FOREIGN PATENT DOCUMENTS

EP    2659929 A2    11/2013
GB    663577 A     12/1951
(Continued)

OTHER PUBLICATIONS

Sweeney, J.K. et al., "Musculoskeletal Implications of Preterm Infant Positioning in the NICU", J Perinat Neonat Nurs 2002; 16(1):58-70.

*Primary Examiner* — Kaylee R Wilson
(74) *Attorney, Agent, or Firm* — Oyen Wiggs Green & Mutala LLP

(57) ABSTRACT

Adverse effects of pain in a premature infant, especially a very or extremely premature infant may be ameliorated by exposing the infant to stimuli comprising one or more of vertical oscillating motion simulating breathing, skin contact with an interface that mimics human skin and exposure to sounds and/or vibrations that simulate heartbeats. A device including a movable platform provides such stimuli within a neonatal intensive care incubator. The device provides simulated maternal breathing through vertical movement at
(Continued)

a rate and speed similar to that experienced by an infant lying upon its mother's chest. It further provides simulated maternal skin interface feel as well as heartbeat sound. These simulated sensory parameters appear to have an innate calming effect upon a preterm infant that reduces the duration and severity of the infant's response to a pain event. The same stimulations may reduce occurrence of below-baseline fluctuations of brain blood oxygen content.

21 Claims, 5 Drawing Sheets

(51) Int. Cl.
*A61M 21/00* (2006.01)
*A61M 16/00* (2006.01)

(52) U.S. Cl.
CPC ..... *A61M 21/0094* (2013.01); *A61G 2210/50* (2013.01); *A61M 16/00* (2013.01); *A61M 2021/0022* (2013.01); *A61M 2021/0027* (2013.01); *A61M 2021/0088* (2013.01); *A61M 2202/0208* (2013.01); *A61M 2205/3368* (2013.01); *A61M 2230/04* (2013.01); *A61M 2230/205* (2013.01); *A61M 2240/00* (2013.01)

(58) Field of Classification Search
CPC ............ A61M 16/00; A61M 2230/205; A61M 2230/04; A61M 2205/3368; A61M 2202/0208; A61M 2021/0088; A61M 2240/00; A61G 11/002; A61G 11/008; A61G 2210/50; A47D 9/02

USPC .......................................... 600/21–22, 26–28
See application file for complete search history.

(56) References Cited

U.S. PATENT DOCUMENTS

| | | | |
|---|---|---|---|
| 3,419,923 A | 1/1969 | Cowan | |
| 3,809,065 A | 5/1974 | Gatts | |
| 3,993,042 A | 11/1976 | Gatts | |
| 4,088,124 A * | 5/1978 | Korner | A61H 1/001 |
| | | | 5/674 |
| 5,037,375 A | 8/1991 | Gatts | |
| 6,540,660 B1 | 4/2003 | Speraw et al. | |
| 6,918,770 B2 | 7/2005 | Odiwo | |
| 6,971,127 B2 | 12/2005 | Richards | |
| 7,475,441 B1 | 1/2009 | Soberal | |
| 2004/0123383 A1 | 7/2004 | Nguyen | |
| 2005/0198739 A1* | 9/2005 | Elkin | A47D 13/08 |
| | | | 5/655 |
| 2005/0215845 A1 | 9/2005 | Mahony et al. | |
| 2008/0098521 A1 | 5/2008 | Westerkamp et al. | |
| 2011/0144416 A1 | 6/2011 | Waddell | |
| 2012/0192874 A1* | 8/2012 | Bolea | A61N 1/3601 |
| | | | 128/848 |
| 2014/0275894 A1* | 9/2014 | Bignall | A61B 5/0084 |
| | | | 600/343 |
| 2014/0330070 A1 | 11/2014 | Anabalon Alamos et al. | |
| 2017/0172411 A1* | 6/2017 | Bloch-Salisbury | |
| | | | A61B 5/6892 |

FOREIGN PATENT DOCUMENTS

| | | |
|---|---|---|
| GB | 2429400 A | 2/2007 |
| WO | 2014091412 A1 | 6/2014 |

* cited by examiner

APPARATUS AND METHODS FOR IMPROVING HEALTH OUTCOMES OF PRETERM INFANTS

CROSS-REFERENCE TO RELATED APPLICATIONS

This application claims priority from U.S. Application No. 62/059,274 filed 3 Oct. 2014 and also U.S. Application No. 62/203,071 filed on 10 Aug. 2015. For purposes of the United States, this application claims the benefit under 35 U.S.C. § 119 of U.S. Application No. 62/059,274 filed 3 Oct. 2014 and entitled PAIN THERAPY METHOD AND DEVICE FOR PRETERM INFANTS and U.S. Application No. 62/203,071 entitled BRAIN BLOOD OXYGEN STABILIZATION METHOD AND DEVICE FOR PRETERM INFANTS filed 10 Aug. 2015, both of which are hereby incorporated herein by reference for all purposes.

BACKGROUND

The normal term of a human pregnancy is in the range of 37 to 42 weeks with 40 weeks being typical. Infants born more than 3 weeks before full term (i.e. at less than 37 weeks of gestation) are called 'premature'.

Approximately one of every eight infants born in the United States is premature. Premature infants tend to be underweight in comparison to full term infants. Premature infants also tend to suffer from various health problems. These health problems can be very complicated. Such health problems may stem from the fact that a premature baby's organs may not yet have developed to the point that the baby can live independently outside of the womb. For example, premature infants often have difficulty breathing and regulating their body temperatures and may have other problems caused by underdevelopment of a range of organs. These problems particularly affect infants born before 35 weeks gestational age. All biological systems in such infants are immature having been previously regulated through the mother's placenta.

Critical biological systems that can be underdeveloped in premature infants include:
the central nervous system (e.g. brain)
the cardiovascular system,
the immune system and
the gastro-intestinal system.

The health problems faced by premature infants tend to vary depending upon how prematurely the infants are born. Infants born in the later preterm (i.e. between 35 and 37 weeks gestation) may look like full term babies. However, even late preterm babies tend to be at greater risk for certain health problems than full term babies.

Infants born at or before 34 weeks of gestation typically lack the ability to suck and swallow in a coordinated manner.

Infants born between 32 and 34 weeks of gestation may be called 'moderately preterm'. Infants born at less than 32 weeks of gestation may be called 'very preterm'. Infants born at or before 28 weeks of gestation may be called 'extremely preterm'.

Infants weighing less than 1500 grams and/or being eight weeks or more premature (i.e. very or extremely premature infants having gestation of 32 weeks or less), can be exceedingly frail and usually require support to stay alive and grow. With their immature biological systems, these infants cannot breathe on their own to maintain normal oxygen levels, regulate their body temperatures, fight infections effectively or feed adequately.

Premature infants are typically held in a neonatal intensive care unit (NICU) where their health may be carefully monitored. Monitoring premature infants often includes blood tests (e.g. to check glucose, oxygen, and bilirubin levels); chest X-rays, and continuous cardiorespiratory monitoring.

Premature infants are often placed in incubators or "isolettes" in which air temperature is controlled. Many incubators also include systems for controlling humidity of the air inside the incubator. Some incubators also include facilities for controlling oxygen content of the air inside the incubator.

An incubator in a NICU may, for example, provide:
delivery of ambient oxygen to help maintain oxygen levels;
a relatively closed volume to exclude environmental dust/pollutants which can cause lung damage;
systems for controlling temperature to help maintain body temperature;
systems for maintaining and controlling humidity to prevent skin breakdown which is linked to increased risk of infection;
a relatively sterile space to help prevent infection; and/or attenuation of some ambient light and noise to allow the infant to rest.

It is challenging to assess whether premature infants are experiencing pain or stress because they may not respond to pain in the ways typical of full-term infants. Some caregivers may take the lack of 'normal' response to painful stimuli to indicate that premature infants are not bothered by pain. The inventors consider that this is a particular problem that is made worse by the fact that premature infants are subjected to frequent procedures that can be painful such as heel pricks to obtain blood for testing. Such painful stimuli cause stress to premature infants. While such stress can adversely affect the infants, the procedures are necessary and it is not generally practical to control this type of pain in premature infants using analgesic drugs. The inventors believe that methods and apparatus that may be used to reduce stress in premature infants may improve health outcomes for those infants.

There remains a need for effective techniques for improving health outcomes for premature infants, especially 'very' and 'extremely' premature infants.

SUMMARY

The present invention has a number of aspects. Without limitation, these aspects include:
apparatus useful in the care of pre-term infants;
uses of such apparatus in the care of pre-term infants;
methods for treating preterm infants;
methods for controlling pain in preterm infants; and
methods for reducing sub-baseline brain blood oxygen content in preterm infants.

While various aspects of the invention may be applied to any pre-term infants, preterm infants having gestational ages of 32 weeks or less and particularly 30 weeks or less may benefit particularly from the inventive apparatus and methods described herein.

One example aspect of the invention provides apparatus for treating premature infants. The apparatus comprises an incubator housing, a warming system comprising a temperature controller connected to control a temperature within the incubator housing and a humidifier connected to maintain a desired humidity level within the incubator housing. A platform is provided within the housing. The platform dimensioned to support an infant. One or more actuators are connected to the platform and are operable to move the platform in at least a vertical direction with an oscillating motion. A controller is connected to control the actuators to move the platform to oscillate in the vertical direction at a frequency in the range of 5 to 25 oscillations per minute. The platform may have a flat unobstructed top surface.

Another example aspect provides apparatus for treating premature infants. The apparatus comprises a premature infant incubator comprising a platform within a housing of the premature infant incubator. The platform is dimensioned to support an infant on a substantially planar upper surface. An actuation system is connected to drive motion of the platform in at least a vertical direction with an oscillating motion. A controller is connected to control the actuation system to move the platform to oscillate in the vertical direction at a frequency in the range of 5 to 25 oscillations per minute.

Another example aspect provides apparatus for treating premature infants. The apparatus comprises a platform insertable into a housing of a premature infant incubator and dimensioned to support an infant on a substantially planar upper surface. An actuation system is connected to drive motion of the platform in at least a vertical direction with an oscillating motion. A controller is connected to control the actuation system to move the platform to oscillate in the vertical direction at a frequency in the range of 5 to 25 oscillations per minute.

Apparatus according to any of the above example embodiments as well as other embodiments described herein may provide various additional features individually or in any combinations. The following paragraphs summarize some such features.

Various options may be provided for controlling operation of the platform. For example apparatus may provide one or more of the following features:
  In some embodiments the apparatus comprises a control which is operable by a user to adjust the frequency of the oscillations of the platform.
  In some embodiments the apparatus comprises a blood oxygen sensor connected to supply a blood-oxygen signal representing blood oxygen content to the controller and the controller is configured to adjust one or both of a frequency and amplitude of oscillation of the platform based on the blood-oxygen signal.
  In some embodiments the apparatus comprises a heart monitor associated with a signal processor configured to process an output signal of the heart monitor signal to yield a HRV signal indicative of heart rate variability wherein the controller is configured to adjust one or both of a frequency and amplitude of oscillation of the platform based on the HRV signal.
  In some embodiments the controller comprises a stored schedule of pain events and the controller is configured to initiate oscillation of the platform in coordination with pain events in the schedule of pain events.

The upper surface of the platform may have features that provide a skin-like interface. For example:
  an upper surface of the platform may comprise a breathable waterproof material such as a flexible EPTFE membrane.
  the upper surface of the platform may be characterized by a durometer on the Shore OO scale.
  a layer of a low durometer material may underlie the breathable waterproof material.

The platform may be controllable to provide levels of displacement and/or acceleration to the infant sufficient to provide beneficial reductions in pain and/or reductions in sub-baseline blood oxygen level fluctuations. In some embodiments:
  the oscillations of the platform have a total vertical displacement in the range of 1 mm to 5 cm at least at a location of the infant's head.
  the oscillations of the platform have a total vertical displacement in the range of 1 mm to 5 cm at a geometric center of the platform.
  the oscillations of the platform have a total vertical displacement in the range of ½ to 2 cm at least at a location of the infant's head.
  the oscillations of the platform have a total vertical displacement in the range of ½ to 2 cm at the geometric center of the platform.

The platform may be constructed so that it is stiff and provides a flat surface for supporting the infant. For example:
  the platform may comprise a stiff generally planar form. The form may, for example, comprise an acrylic material. The acrylic material may be vacuum formed.
  the platform may be formed with a peripheral skirt which may stiffen the platform.

The apparatus may comprise a sound and vibration transducer. In such embodiments the controller may comprise a memory storing pre-recorded digitized heartbeat sounds or a sound generator configured to generate simulated heartbeat sounds. The controller is connected to drive the sound and vibration transducer with the recorded heartbeat sounds from the memory or the simulated heartbeat sounds from the sound generator. The sound and vibration transducer may be mounted to the platform (e.g. under the platform).

The platform and/or incubator housing may include features to facilitate X-ray imaging or other forms of imaging of the infant. For example, apparatus may have one or more of the following features:
  the platform is X-ray transparent.
  indicia on a top surface of the platform indicates an area of an X-ray transparent portion of the platform.
  a compartment provided under the platform is dimensioned to receive an X-ray film cartridge or a digital X-ray image sensor. The compartment may comprise, for example, a pull-out drawer or a slot.

Various arrangements may be provided to drive the platform. Preferably the system for driving the platform operates quietly (e.g. such that a sound level at the location of the infant does not exceed 60 dB). In some example arrangements:
  one or more actuators are connected directly between the incubator housing and the platform.
  the platform is suspended relative to the incubator housing by a bias mechanism (which may, for example, comprise one or more springs) and one or more actuators are operable to displace the platform upwardly and downwardly relative to an equilibrium position of the platform.
  one end of the platform may be pivotally mounted for rotation about a pivot axis and one or more actuators may be connected to rotate the platform about the pivot axis.
  actuators may be connected to lift and lower the platform while preserving an orientation of the top surface of the platform.
  one or more actuators may be located in all or in part outside of an incubator housing and may be connected to move the platform within the incubator housing.

the platform may be mounted to an incubator housing and the one or more actuators may be connected to oscillate the incubator housing and the platform in the vertical direction. In such embodiments the platform may be fixedly mounted to the incubator housing.

Another example aspect provides use of apparatus as described herein for controlling pain in preterm infants and/or for reducing sub-baseline fluctuations of brain blood oxygen associated with a scheduled pain event in preterm infants.

Another example embodiment provides a method for treating a preterm infant, The method comprises placing the infant on a platform; prior to a pain event commencing moving the platform to oscillate substantially vertically at a frequency in the range of 5 to 25 oscillations per minute; and continuing vertically oscillating the platform after the pain event.

Another example embodiment provides a method for controlling pain in a preterm infant, The method comprises: prior to a scheduled pain event, placing the preterm infant on a platform and commencing moving at least the infant's head substantially vertically by reciprocating the platform at a frequency in the range of 5 to 25 oscillations per minute; subjecting the infant to the pain event; and continuing vertically oscillating the platform after the pain event at a frequency in the range of 5 to 25 oscillations per minute, the oscillations before and after the pain event having an amplitude sufficient to cause in the infant a reduction in stress as demonstrated by an increase in heart rate variability of the infant.

Another example embodiment provides a method for reducing sub-baseline fluctuations of brain blood oxygen concentration in a preterm infant. The method comprises: prior to a scheduled pain event, placing the preterm infant on a platform and commencing moving at least the infant's head substantially vertically by reciprocating the platform at a frequency in the range of 5 to 25 oscillations per minute; subjecting the infant to the pain event; and continuing vertically oscillating the platform after the pain event at a frequency in the range of 5 to 25 oscillations per minute. The oscillations before and after the pain event have an amplitude sufficient to cause in the infant a reduction in sub-baseline fluctuations of brain blood oxygen concentration as demonstrated by non-invasive transcranial NIRS measurements of the blood oxygen concentration in the infant's brain.

Methods according to any of the above example embodiments as well as other embodiments described herein may provide various additional features individually or in any combinations. The following paragraphs summarize some such features.

The methods may be performed on preterm infants at various gestational ages. Some particular benefits may be achieved where the infant has a gestational age of not more than 32 weeks or not more than 30 weeks. In some embodiments the infant has a weight of 1500 g or less or a weight of 1200 g or less.

The oscillations may have levels of displacement and/or acceleration sufficient to provide beneficial reductions in pain and/or reductions in sub-baseline blood oxygen level fluctuations. In some embodiments:

the oscillations have a total vertical displacement in the range of 1 mm to 5 cm at least at a location of the infant's head.

the oscillations have a total vertical displacement in the range of 1 mm to 5 cm at a geometric center of the platform.

the oscillations have a total vertical displacement in the range of ½ to 2 cm at least at a location of the infant's head.

the oscillations have a total vertical displacement in the range of ½ to 2 cm at the geometric center of the platform.

The oscillations may be performed at least in time periods before and/or after the pain event. For example, for at least 15 minutes before the pain event and/or for at least 5 minutes after the pain event. In some embodiments the oscillations are maintained substantially continuously for extended periods of time (hours or days) during which a number of pain events may occur. In some embodiments oscillation and/or delivery of heart sounds is provided for at least 9 or 10 hours of a 12-hour period.

Various options may be provided for controlling stimulation of the infant by oscillations and/or sounds. For example methods may provide one or more of the following features:

In some embodiments the methods set frequency and/or amplitude of the oscillation based on receiving an input at a control.

In some embodiments the methods comprise setting one or both of a frequency and amplitude of the oscillation based on a blood-oxygen signal.

In some embodiments the methods comprise setting one or both of a frequency and amplitude of the oscillation based on a HRV signal.

In some embodiments the methods comprise setting one or more of a frequency, character and amplitude of heartbeat sounds based on a HRV signal.

In some embodiments the methods comprise setting one or more of a frequency, character and amplitude of heartbeat sounds based on a measure of blood oxygen level in the infant.

In some embodiments the methods control the oscillation based on a stored schedule of pain events. for example, oscillation may be automatically initiated in advance of a scheduled pain event such as a blood test.

In some embodiments the methods may include performing a positioning protocol on the infant. The positioning protocol may comprise positioning the infant in supine, sidelying and prone positions on the platform.

Further aspects and example embodiments are illustrated in the accompanying drawings and/or described in the following description.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

This invention has a number of aspects. One aspect provides incubators for preterm infants. An incubator is fitted with apparatus for providing sensations to a premature infant. The sensations include rising and falling motion similar to what an infant would experience lying on his or her mother's chest as the mother breathes naturally. The inventors have discovered that use of apparatus which provides such sensations can reduce the responses of premature infants to pain, as well as to stabilize blood oxygen levels (particularly brain blood oxygen levels) in premature infants.

Another aspect of the invention provides apparatus for providing sensations to premature infants. The apparatus may be placed inside a neonatal intensive care incubator. Another aspect of the invention provides methods for treating premature infants, especially very or extremely premature infants, to reduce pain response, reduce stress, and/or improve the uniformity of brain blood oxygen concentration.

Figure 1:
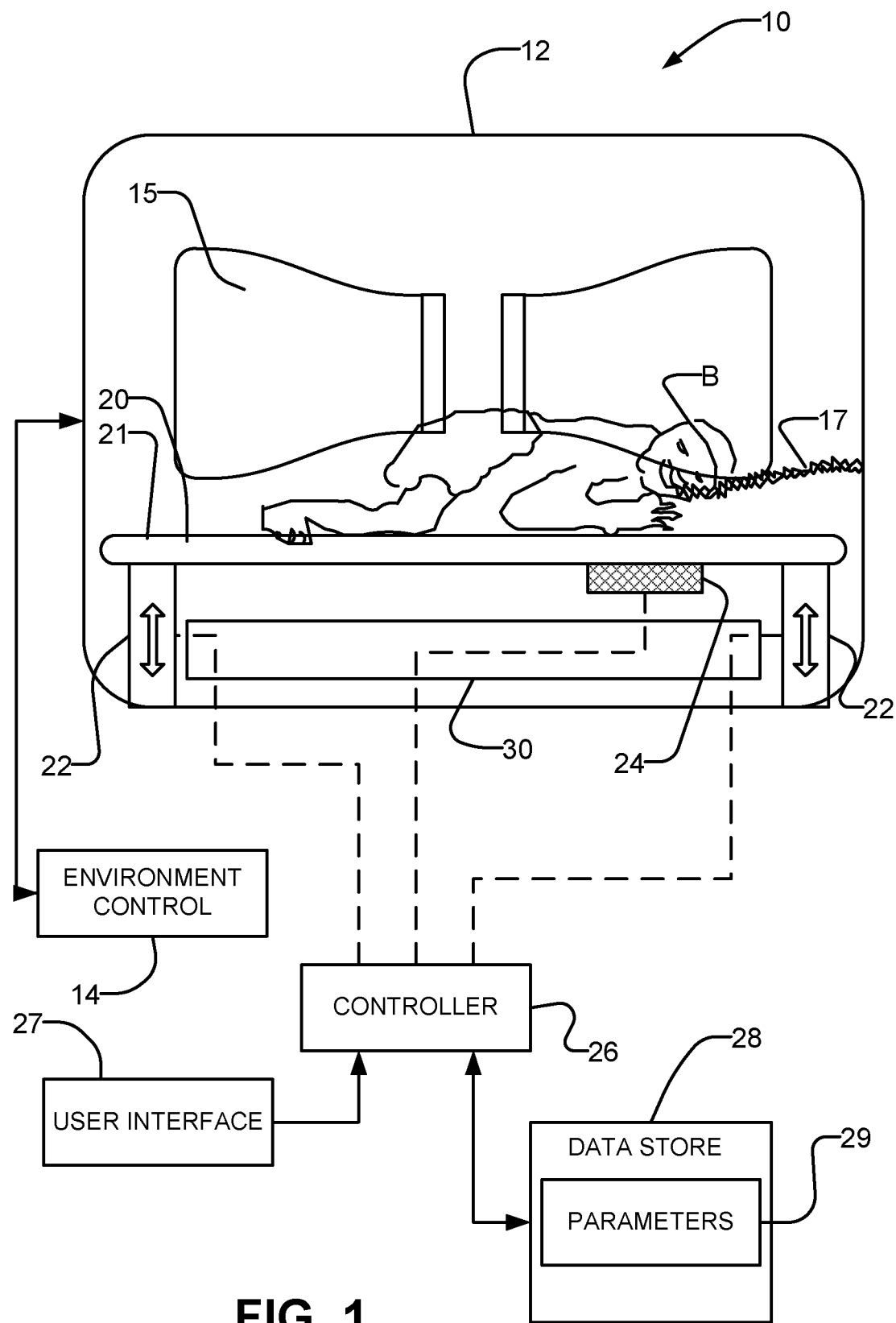
FIG. 1 is a partially schematic side elevation view of an incubator according to an example embodiment of the invention.

FIG. 1 illustrates an example incubator 10. Incubator 10 may have a range of features that are common or standard in NICU incubators. In the illustrated embodiment incubator 10 comprises a housing 12. A temperature and humidity control system 14 maintains desired temperature and humidity levels within housing 12. Doors 15 are provided to facilitate access to an infant B lying within housing 12. An air supply tube 17 may carry air having a regulated oxygen content to infant B from a ventilator, continuous positive airway pressure (CPAP) machine, or oxygen supply.

Figure 5:
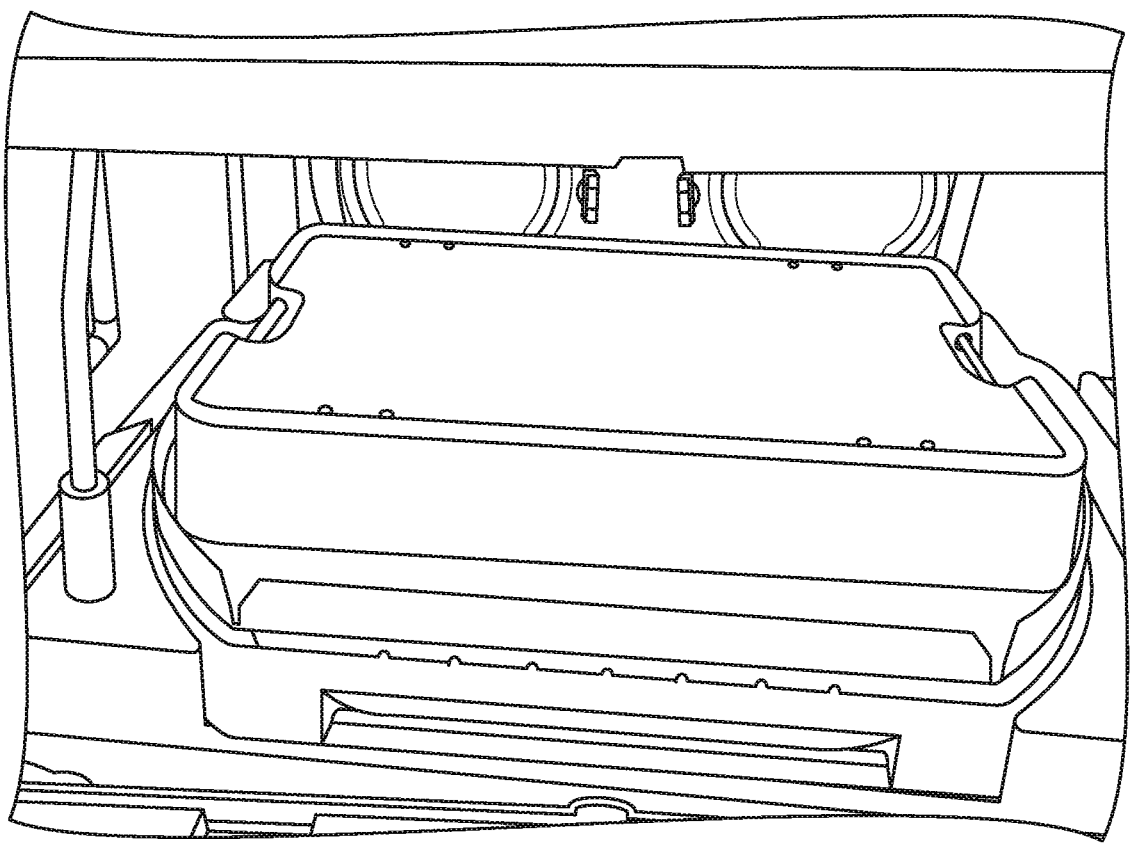
FIG. 5 is a photograph showing an example platform form in an incubator. The surface coverings have been removed from the form in this photograph.

Baby B lies on a surface 21 of a platform 20. Surface 21 provides a simulated skin interface that allows for transpiration of moisture (e.g. sweat) of the baby B. Surface 21 mimics the interfacial feel of human skin. Surface 21 may be embodied, for example, by a low durometer (very soft) material disposed above a stiff form made, for example, of acrylic. An example form is shown in FIG. 5. The FIG. 5 embodiment includes a skirt extending around a periphery of the form.

The durometer of the material of surface 21 may, for example, be measured on the Shore OO scale. The measurement may be made according to the ASTM D2240-00 testing standard. The OO scale measures the softness of materials that are indented in the range of up to 0.1 inches (2.54 mm) by a spherical indenter having a radius of 1.20 mm under an applied force of 1.11 Newtons (113 grams force).

In some embodiments platform 20 comprises a stiff vacuum-formed acrylic shell. The shell is predominantly flat in at least the area that supports infant B in normal use. Providing a flat and open area for supporting an infant B is advantageous for facilitating positioning protocols to be performed on infant B as discussed below. All materials used in apparatus 10 should be fully cured before use and selected to avoid materials that release gases (e.g. by off-gassing) that could be harmful to infant B.

Examples of materials that may be used to provide surface 21 include: silicone rubber, "memory foam" (e.g. viscoelastic polyurethane), sorbothane, natural rubber, and other similar sterilizable elastic polymers. The materials of surface 21 preferably do not affect X-rays significantly. At least some gels can significantly absorb X-rays. Surface 21 preferably does not include such gels at least in the portion of platform 20 that supports infant B in normal use. A layer of such material may be covered with a breathable covering to provide surface 21. For example, in some embodiments, surface 21 comprises a soft material covered by a breathable synthetic cloth. The cloth may, for example be a nylon cloth. In some embodiments the cloth is coated with a breathable but liquid-blocking material such as EPTFE (expanded polytetrafluoroethylene). EPTFE is soft, flexible and porous. EPTFE is permeable to air, yet watertight at low pressures.

Platform 20 is movable by one or more actuators 22 which operate under control of a controller 26. These motions are transferred to infant B who is supported on platform 20. Actuators 22 may be controlled to move platform 20 to effect a simulated maternal breathing motion. For example, platform 20 may be oscillated in a substantially vertical manner, at a frequency in the range of 5 to 25 oscillations per minute, preferably 10 to 18 oscillations per minute. Depending on how platform 20 is actuated, the displacement of the platform may be uniform at all locations on the platform or may vary from place-to-place on the platform. Displacement, of platform 20 at the position of the infant's head may, for example, be in the range of 0.1 to 5 cm. Preferably, the range of motion of platform 20 in the vertical direction at the position of the infant's head is in the range of 0.5 to 2 cm.

The oscillating motion of platform 20 may optionally include a short dwell at either or both of the maximum and minimum displacements of platform 20. In some embodiments position and/or velocity of platform 20 are controlled by a servo controller. In some embodiments, acceleration of platform 20 is controlled such that acceleration of platform 20 smoothly increases and decreases during the oscillation. In some embodiments the oscillating motion of platform 20 is sinusoidal or approximately sinusoidal. In some embodiments acceleration of platform 20 is limited to a value not exceeding about 0.4 in/sec$^2$ (about 1 cm/sec$^2$).

Such an oscillating motion applies a periodic acceleration to the infant. Where the imparted motion is sinusoidal or nearly so the maximum velocity, $v_{max}$, is given by $v_{max}=2\pi Df$ where D is the displacement amplitude (½ of the total displacement of the platform) and f is the frequency. In the above examples, $v_{max}$ is in the range of $2\pi \times 0.1$ cm×½×5 min$^{-1}$=1.57 cm/min to $2\pi \times 5$ cm×½×25 min$^{-1}$=392 cm/min with a preferred range of 15.7 cm/min to 113 cm/min. The maximum acceleration, $a_{max}$, is given by $v_{max}=D(2\pi f)^2$ which, for the above examples is in the range of 100 cm/min$^2$ to 123000 cm/min$^2$ with a preferred range of about 2000 cm/min$^e$ (about ½ cm/sec$^2$) to about 25500 cm/min$^e$ (about 7 cm/sec$^2$).

Actuators 22 may be of any suitable type or types. Actuators 22 may drive different types of mechanical motion, may be powered by different power sources and/or may generate motion according to different physical principles and/or mechanical arrangements. For example, actuators 22 may comprise linear actuators, rotary actuators, or pivoting actuators. Actuators 22 may be powered by electricity (e.g. linear actuators, electric motors, servo motors), pressurized gas (e.g. pneumatic cylinders, inflatable bladders, pneumatic motors) or pressurized fluid (e.g. hydraulic cylinders or hydraulic motors). Actuators 22 may directly move platform 20 to rise and fall or may be coupled to move platform 20 using any suitable linkages. Examples of linkages include screws, rack and pinion mechanisms, pivoting links, and/or crank mechanisms.

Actuators 22 may be selected to be compatible with the environment of an intensive care nursery. Preferably, actuators 22 operate quietly such that the total sound level within incubator 10 does not exceed approximately 60 decibels. Sounds louder than this can harm hearing in premature infants (see e.g. Graven, 2000 *J Perinatol.* 2000 December; 20(8 Pt 2):S88-93). Electrical actuators and controls, if used, may satisfy requirements for limited emissions of electromagnetic interference.

In some embodiments a plurality of actuators 22 are operated in concert to raise and lower platform 20. For example, three or more actuators 22 may be spaced apart around a periphery of platform 20. The actuators 22 may be extended and retracted together to cause platform 20 to rise and fall as described above.

In an alternative embodiment, platform 20 is pivotally mounted for rotational movement about a horizontal axis near one end of platform 20. In such embodiments the infant would typically be oriented such that his or her feet are toward the pivoting end of the platform. One or more actuators 22 may be operated to pivot platform 22 about the horizontal axis with the result that the other end of platform 20 moves with the desired substantially-vertical motion at the nominal position where an infant's head would be placed.

In some embodiments (including embodiments with any of the above actuator arrangements) platform 20 is supported by a bias mechanism which may comprise, for example, one or more springs such that actuators 22 drive platform 20 both up and down from an equilibrium position. The bias mechanism may be set such that platform 20 settles at a desired average height when carrying an infant weighing, for example, 1.5 kg. In some embodiments the bias mechanism is adjustable to fine tune the equilibrium positions for different infants. Where the weight of platform 20 and infant B is primarily supported by such a bias mechanism the mechanical work performed by actuators 22 and the forces exerted by actuators 22 in oscillating platform 20 may be reduced. These factors may, in turn, reduce the amount of heat dissipated by actuators 22 and/or the noise made by actuators 22 as well as improve the energy efficiency of the apparatus.

In some embodiments, platform 20 is arranged to prevent fluids that may be present in the vicinity of infant B from entering the space below platform 20. For example, platform 20 may be shaped to form a rim around its edges. Any such shaping should preferably avoid a configuration which can trap $CO_2$ in the vicinity of the infant's head. $CO_2$ can adversely affect breathing rate and drive to breathe.

In some embodiments platform 20 is arranged so that it is tilted. In some embodiments a degree of tilt of platform 20 is adjustable either stepwise or continuously. Platform 20 may comprise a drain located in an area that is low when the platform is tilted.

In some embodiments the clearance between platform 20 and incubator shell 12 is such that there are no pinch points between platform 20 and incubator shell 12. This may be achieved by providing either a very small clearance or a large enough clearance. For example, in some embodiments the clearance between platform 20 and incubator housing 12 is approximately 1 cm, which is generally large enough to avoid pinching. Such a gap is also large enough to allow air to flow as platform 20 is oscillated.

In some embodiments a flexible bellows extends between platform 20 and incubator shell 12 and/or a surround of platform 20 is attached to move together with platform 20 such that there is no pinch space around the periphery of platform 20 that could pinch any part of the infant B or equipment such as ventilator tubes, ECG electrode wires, IV tubes or the like. The flexible bellows, if present, is optionally a continuation of a cover of platform 20. These constructions may also be advantageous for attenuating sounds from actuators 22 or other mechanisms under 20 at the location of infant B on top of platform 20. In embodiments where there is little clearance between platform 20 and incubator housing 12 and/or a bellows or the like impedes airflow around platform 20 then alternative vents or openings may be provided to allow for airflow into and out of the space below platform as platform 20 is moved.

Positioning of a preterm infant has important musculoskeletal implications. Skeletal structures are highly plastic and responsive to body positioning such that movements and postures received or imposed in the NICU contribute to the shaping of the infant's body, joints and skull. It is desirable to apply positioning programs to provide for proper development. Such positioning programs may include positioning the infant in supine, sidelying and prone positions, each with specific aims for musculoskeletal development (See: Jane Sweeney, "Musculoskeletal Implications of Preterm Infant Positioning in the NICU", *Journal of Perinatal and Neonatal Nursing*, Apr. 23, 2002). Platform 20 may be configured to facilitate such positioning. In the illustrated embodiment, platform 20 is large enough to position a preterm infant in any of the above postures and is free of obstacles that would obstruct NICU caregivers from providing such positioning programs.

In the illustrated embodiment, a sound and/or vibration transducer, such as a speaker 24, is provided in incubator 10. For example speaker 24 may be mounted on platform 20 to convey sounds and vibrations directly to an infant lying on surface 21. Speaker 24 may be controlled to emit sounds and vibrations which are reminiscent of the intrauterine environment. For example, speaker 24 may be controlled to emit recorded or simulated heartbeat sounds. Controller 26 may include a memory storing a pre-recorded heartbeat sounds and/or a heartbeat simulator that synthesizes sounds having the periodicity and timbre like those of heartbeat sounds (as present in the intrauterine environment).

Platform 20 may optionally provide one or more additional features such as:

- an adjustable tilt so that medical caregivers may adjust the height of one end of platform 20 to facilitate easier breathing by the infant (e.g. tilt the platform such that the infant's head is higher than his or her feet). Such a tilting mechanism may be provided by a mechanism arranged to adjust and fix the height of one end of the platform (e.g. a ratchet, cam-lock, screw, movable block, wedge, hook etc.). an opposing end of platform 20 (preferably the foot end) may be hinged.
- a lock to hold platform 20 against moving. The lock may be engaged to create a solid backing surface for the infant if caregivers must perform cardio-pulmonary resuscitation (CPR). In some embodiments the lock is integrated with a drive mechanism that actuates oscillation of platform 20. For example the lock may be implemented by electrically holding an electric motor that actuates the drive mechanism, actuating a brake in the drive mechanism, closing a valve to hold actuators of a hydraulic drive mechanism in a current position or the like. In other embodiments a mechanical lock is provided. In some embodiments, pressing down on platform 20 with more than a threshold amount of force locks platform 20 in place. The same action may disable operation of the actuators that drive motion of platform 20. For example, if platform 20 is pressed down firmly spring-loaded catches may automatically engage between platform 20 and incubator housing 12 to lock platform 20 in place. At the same time a micro switch, optical sensor or the like may sense that platform 20 has been locked and signal controller 26 to inhibit oscillation of platform 20.

a load cell or pressure sensor arranged to measure a weight of an infant on platform 20.

markings to assist in positioning infant B. For example, platform 20 may be marked to indicate a 'normal' position for an infant, a desired location of the infant's head, the extent of an area of platform 20 that is X-ray transparent and/or suitable for other medical imaging modalities and/or a location of speaker 24. It may be desirable to place the infant's head close to but not directly on top of speaker 24.

markers for use in medical diagnostics (e.g. a ruler and/or one or more markings visible in X-ray images).

Controller 26 includes a user interface 27 which allows a user to alter operating parameters used by controller 26. For example, interface 27 may provide controls that allow a user to adjust the rate at which platform 24 is moved to simulate breathing (i.e. a rate of oscillation of platform 20). Other controllable parameters may include one or more of the amplitude of motions of platform 20, the pattern of motion of platform 20 (e.g. does platform 20 merely move up and down in a vertical motion or is it optionally also rocked from side-to-side or head to toe), heartbeat sound, amplitude, and frequency delivered by speaker 24.

User interface 27 may additionally include controls that allow a caregiver to enable operation of the apparatus in advance of a 'stress' (or pain) event for infant B (e.g. by setting a timer to turn on oscillation of platform 20 at a certain time and/or for a certain duration). In some embodiments user interface 27 optionally provides controls which enable and/or set parameters for automatic control of apparatus 10 in response to measurements of physiological conditions of infant B. Such automatic control may incorporate a feedback mechanism using as an input physiological parameters that may comprise, for example, one or more of HRV and blood oxygen concentration.

In the illustrated embodiment, a data store 28 contains parameters 29 which may include parameters set by a user by way of user interface 27 and/or other parameters that affect the operation of incubator 10.

Preterm infants may be highly fragile, especially those who are very or extremely premature, and may require diagnostic imaging tests such as X-rays. Incubator 10 may be designed such that lift mechanisms (e.g. actuators 22 and any linkages) are located peripherally in incubator 10. Platform 20 may be substantially transparent to X-rays (e.g. the materials of which platform 20 is constructed may be chosen to have radio-transparency sufficient to enable imaging radiation, such as X-rays, to pass through without adversely affecting X-ray images. Further, at least the area of platform 20 which supports infant B is preferably uniform and planar to minimize any distortion of X-ray images by platform 20.

In some embodiments a compartment 30 (e.g. a space or drawer) is provided between the bottom of incubator 10 and platform 20. Compartment 30 may be dimensioned to receive image-receiving plates, such as a digital X-ray sensor or a cartridge holding X-ray film. With this arrangement, diagnostic images of an infant on platform 20 may be taken without requiring the infant to be removed from incubator 10. The top of incubator housing 12 may include an X-ray transparent and non-distorting window (e.g. a planar portion of the incubator housing) such that the head of an X-ray machine may be positioned above and outside incubator 10 to image infant B. In some embodiments incubator 10 includes a compartment or slot into which an image—receiving plate may be inserted vertically for the purpose of obtaining lateral X-rays of infant B. In such embodiments X-rays may be delivered laterally through an open porthole in incubator housing 12. Motion of platform 20 may be discontinued while X-rays are being taken.

Platform 20, and its associated mechanisms, may be tightly integrated in the construction of incubator 10. For example, actuators 22 may be attached to housing 12 of incubator 10, platform 20 may replace and/or be integrated with bottom plate of incubator 10. In some embodiments actuators 22 cause an entire incubator housing within which infant B is located to oscillate vertically. In such embodiments platform 20 may be fixed to the oscillating incubator housing. This construction may have one or more advantages such as:

eliminating any problems that could result from gaps between a moving platform and a fixed incubator housing, providing improved isolation of infant B from sounds made by actuator(s) 22, cost-effective construction, improved control of the airflow within the incubator/ environment surrounding the infant.

easy cleaning.

In some embodiments, controller 26 is integrated with controllers for other functions of an incubator. For example, controller 26 may provide a single interface which allows a user to control overall operation of an incubator including temperature, humidity, motion of platform 20, and sounds/ vibrations delivered to an infant.

In alternative embodiments, platform 20, and its associated mechanism, is provided as a stand-alone device that may be placed inside a pre-existing neonatal incubator. Where platform 20 and its associated mechanisms are designed to be used with an existing neonatal incubator it is generally preferred that platform 20 and its associated mechanism have a thickness of about 7 cm or less above the top of the incubator bottom plate (with platform 20 at the low-point in its movement). Most existing incubators have dimensions ample enough to accept apparatus of about 7 to 8 cm in thickness without imposing ergonomic constraints on medical staff/parents reaching through portholes of the incubator to care for the infant when the platform is stationary or in motion.

The inventors have discovered that stimulation, as provided by apparatus 10, can significantly reduce the stress level of premature infants. Such stimulation can also provide very significant reduction in the sensitivity of the infants to pain. By providing such stimuli, adverse effects of painful events such as pricks to remove blood for testing may be reduced. These benefits are achieved in premature infants born at a gestational age of 36 weeks or less. These benefits may be particularly important for premature infants born at a gestational age of 30 weeks or less.

A pilot clinical trial of a prototype apparatus that provided stimuli as described above (e.g. vertical oscillation at a frequency typical of breathing in an adult human, sounds and vibrations typical of the heartbeat of an adult human and interfacial contact with a surface similar to human skin) showed that the physiological pain response of preterm infants exposed to such stimuli is significantly reduced when compared to the current standard of care, both in length and severity. In a method according to an example embodiment a preterm infant (having a gestational age of 36 weeks or less), in some embodiments an infant having a gestational age of 30 weeks or less, is positioned on platform 20 before, during and after an event that may cause pain to the infant, such a blood sampling from a heel prick. The current standard of care to mitigate such pain is for a nurse (or parent) to provide facilitated tucking, which can be described as holding the infant in the arms of the nurse and providing moderate constraining pressure upon the infant during and for a short time immediately after the pain event.

A pilot study of 9 preterm infants with a mean gestational age of 29 weeks and mean age of 25 days, was conducted during routine blood collection procedures. The infants were randomly selected to be in a control group who received facilitated tucking or a test group who received stimulation by way of the prototype device (simulated maternal simulation).

Heart rate variability (HRV) was measured for each of the infants during each of a plurality of periods. A baseline period, a heel prick period and a recovery period. Baseline period is the two-minute period directly preceding the skin breaking for the blood test. Heel prick period is the two-minute period directly after the skin breaking for the blood test. Recovery period is the two-minute period directly after the last contact by the lab technician who completed the blood test. The person who selected these data for analysis did not know what treatment group the HRV data came from so as to avoid bias during the analyses.

HRV provides a measure of stress. HRV is calculated by measuring multiple values of the inter-beat interval heart (the interval between consecutive beats of a person's heart) over a test interval and applying a mathematical operation to these values. The inter-beat interval of a person's heart can vary widely and an accepted measure of this is HRV. In particular, researchers have found, using frequency domain methods (e.g., Fast Fourier Transform), that the power within frequency bands of the HRV can be used to determine stress.

For this study, power spectral estimates of HRV were quantified using the area (power) of the spectrum in a high frequency region of the HRV spectrum (0.15-0.80 Hz region for neonates). HRV may be measured in milli-seconds squared per Hertz. HRV HF power is generally considered to be a direct measure of parasympathetic (PS) nervous system activation and is inversely proportional to stress.

The heart rate signals were recorded using a single-lead surface ECG (lead II) (Biopac, Ca). Continuous ECG signals were digitally sampled at 360 Hz using a specially adapted portable computer system. Custom physiological signal processing software (Mindware, USA) was used to acquire, process and analyze the data. HRV data was acquired in 2-minute blocks before, during and after blood collection.

As noted above, HRV serves as a direct measure of parasympathetic activation. During a baseline period (prior to heel prick), infants on the prototype device had 88% better parasympathetic activation (were less stressed) as indicated by the higher HF HRV values than infants in the Control group. In addition, PS activation (stress reduction) at the time a blood was taken by a heel prick was 43% greater for infants on the prototype device than for infants in the control group. During the recovery period, PS activation was 73% better for infants on the prototype device than for infants in the control group. These findings demonstrate that a method which involves delivering stimuli to premature infants as described herein is effective for pain and stress reduction in the infants, particularly surrounding painful events.

TABLE 1

Table 1 provides a summary of the pilot test data. Results of Pilot Trial using Invented Devices vs. standard of care: Heart Rate Variability – High Frequency Power

| HRV:HF Power $(ms^2/Hz)$ | | Baseline | Heel Prick | Recovery |
|---|---|---|---|---|
| Control Group 1 (N = 4) | Mean | 5.82 | 2.02 | 3.73 (N = 3)* |
| Invented Device Group 2 (N = 5) | Mean | 45.84 | 3.56 | 13.82 |
| Difference | | 40.01 | 1.54 | 10.09 |

*One infant with significant outlier data removed.

Figure 2:
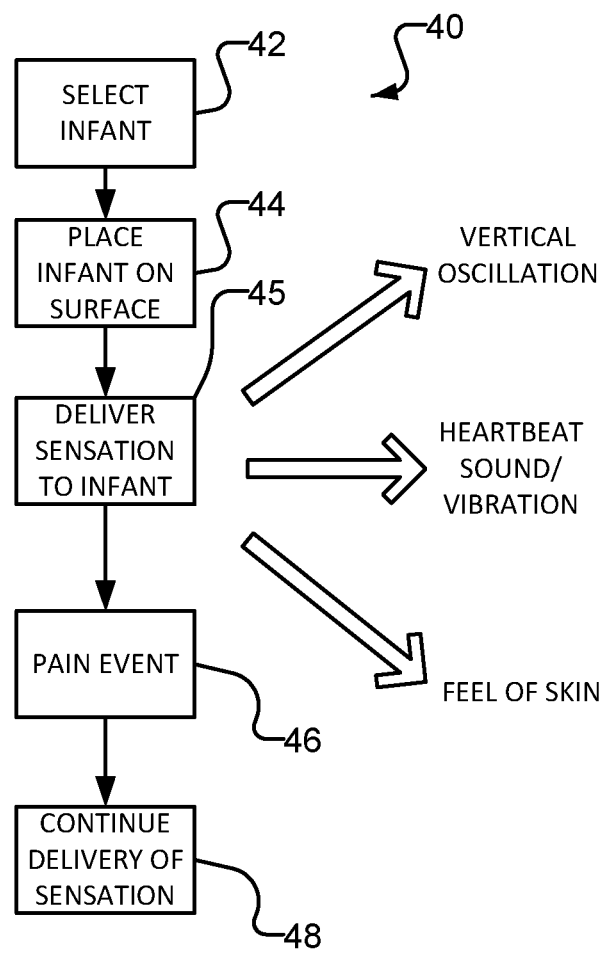
FIG. 2 is a flow chart illustrating a method according to an example embodiment.

In one version of the prototype device, movement of the platform was caused by a pneumatic drive mechanism. The pneumatic drive mechanism provided the lifting forces required to simulate maternal breathing. The pneumatic drive system included a source of pressurized gas, a system of control valves, and pneumatic lift pistons located within an incubator. The control valves were operated to cause the lift pistons to reciprocate the platform up and down in a generally vertical direction. This is one example of a case where power for actuating movement of platform 20 is provided and controlled from outside of incubator 10. Another version of the prototype device provided a rotary motor connected to drive two shafts synchronized to rotate together by means of a toothed belt. Each of the shafts drove rotation of a cam which caused the platform to move vertically. The rotary motor was located outside the incubator and the motion was transmitted to the shafts via a cable, such as one commonly used for steering mechanisms. The platform in the prototype devices has a height of 6.5 cm, a width of 35.5 cm, and a length of 56 cm FIG. 2 illustrates a method 40 according to an example embodiment of the invention. Method 40 stimulates a preterm infant with stimulations which simulate maternal breathing, skin-to-skin interface, and maternal heartbeat.

Method 40 begins by selecting a preterm infant in block 42. In some embodiments the infant has a gestational age of not more than 32 weeks and/or a weight of less than 1500 grams. In block 44, the infant is placed in a platform (such as platform 20 of incubator 10).

In block 45 the platform is operated as described above. The infant's skin is in contact with a material on the upper surface 21 of platform 20 which simulates the feel of maternal skin. Platform 20 is driven to reciprocate up and down at a tempo reminiscent of maternal breathing (e.g. at a frequency in the range of 5 to 25 oscillations per minute, preferably 10 to 18 oscillations per minute with a displacement at least at the position of the infant's head in the range of 0.1 to 5 cm, preferably 0.5 to 2 cm). The infant's head is typically centered on the platform about 14 cm from the edge of one end of the platform (nominally the 'head end') while the platform is being oscillated.

Optionally, sounds and vibration are transmitted to the infant by way of speaker 24 at a frequency or frequencies characteristic of the maternal heartbeat. Oscillation of platform 20 is preferably commenced at least 15 minutes before a pain event. Platform 20 may be oscillated continuously for extended periods.

In block 46, the infant is subjected to a pain event, such as a prick for drawing blood for tests. In block 48, stimulation of the infant is continued as in block 45. Oscillation of platform 20 is preferably continued for at least 5 minutes after a pain event.

Without being bound to any particular theory regarding why method 40 is effective, the inventors consider that method 40 may additionally help to regulate breathing rates in preterm infants thereby reducing periodic breathing (apnea), a condition associated with reduced oxygen levels in premature neonates. In addition, by increasing parasympathetic heart rate variability method 40 may increase acetylcholine (a key neurotransmitter secreted during parasympathetic heart rate regulation) which has a secondary anti-inflammatory effect.

Preterm infants are born with immature lungs and cannot provide adequate oxygenated blood to their organs. As a result, while in intensive care, they receive supplemental ventilation and oxygen. These treatments induce inflammation in the lung tissue leading to a chronic lung condition called bronchopulmonary dysplasia (BPD). Respiratory distress and BPD are the leading causes of death in premature neonates. Thus, any treatment which reduces inflammation may reduce the risk of developing BDP and death. Method 40 may be effective to reduce inflammation through stimulation of the parasympathetic system/increase in acetylcholine.

In addition to the above, the inventors have discovered that the brain-blood-oxygen level in premature infants is highly variable during and after a pain event, such as a routine blood sample collected from a heel-prick. Fluctuations in the blood oxygen level in the brain of a preterm infant can be significant, ranging from 20% above to almost 40% below baseline. Such fluctuations may last for an extended period of time (e.g. 10 to 15 minutes). This places the infant at risk for either intracranial hemorrhage or anoxia, both of which can lead to short- and long-term developmental issues for the infant.

This observation was made using a Near Infra-Red Spectroscopy (NIRS) machine with a prototype probe specifically designed in a small size for use with premature infants. The probe was strapped in place over the infants' scalps and provided direct measures of brain blood oxygenation. Brain blood oxygenated- and deoxygenated-hemoglobin concentrations ([O2Hb], [HHb]), as well as two calculated values, total hemoglobin concentrations at HIA=[O2Hb+HHb]) and local brain tissue saturation were monitored in ten premature infants. The probe was positioned on each infant's skull to obtain direct brain blood measurements. These observations indicated wide variations in blood oxygen during and after a pain event. In one infant these changes persisted for 10 to 15 minutes. In addition, results of the NIRS measurements correlated highly with a valid and reliable behavioral pain scale (in this case the Behavioral Indicators of Infant Pain—"BIIP" scale).

Figure 3:
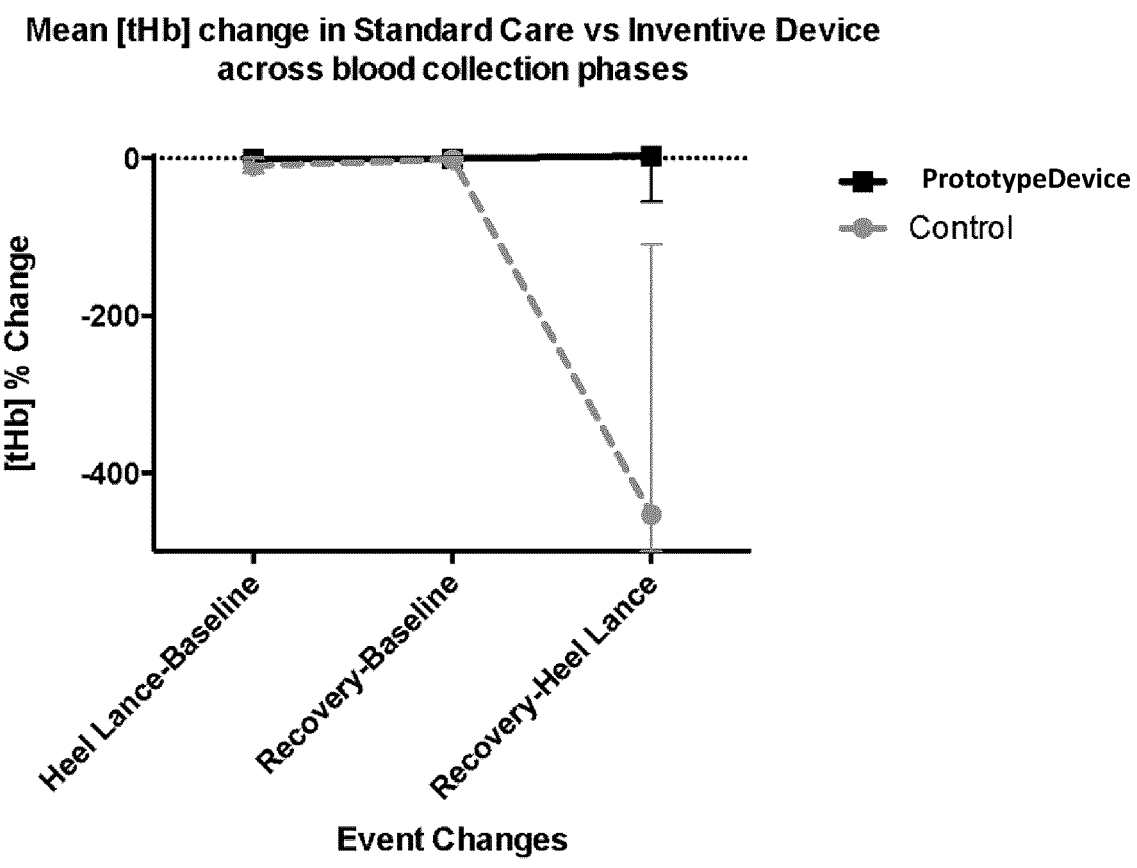
FIG. 3 is a plot illustrating brain blood oxygen concentration fluctuations in infants subjected to heel pricks for blood collection.

Method 40 may be effective to reduce the magnitude and/or duration of fluctuations of brain blood oxygen content below baseline that may be caused by pain events in premature infants. In general, the use of apparatus as described herein may result in better brain-blood-oxygen stability for such infants while they reside in neonatal intensive care incubators. Improved brain-blood-oxygen stability would tend to improve developmental outcomes for these infants, and should lead to a wide range of benefits for these infants, their parents, and significant cost reduction for the health-care system. FIG. 3 is a graph comprising curves showing the incidence of sub-baseline brain blood oxygenation fluctuations for infants treated using the prototype device and infants in a control group treated using the current standard of care.

Figure 4:
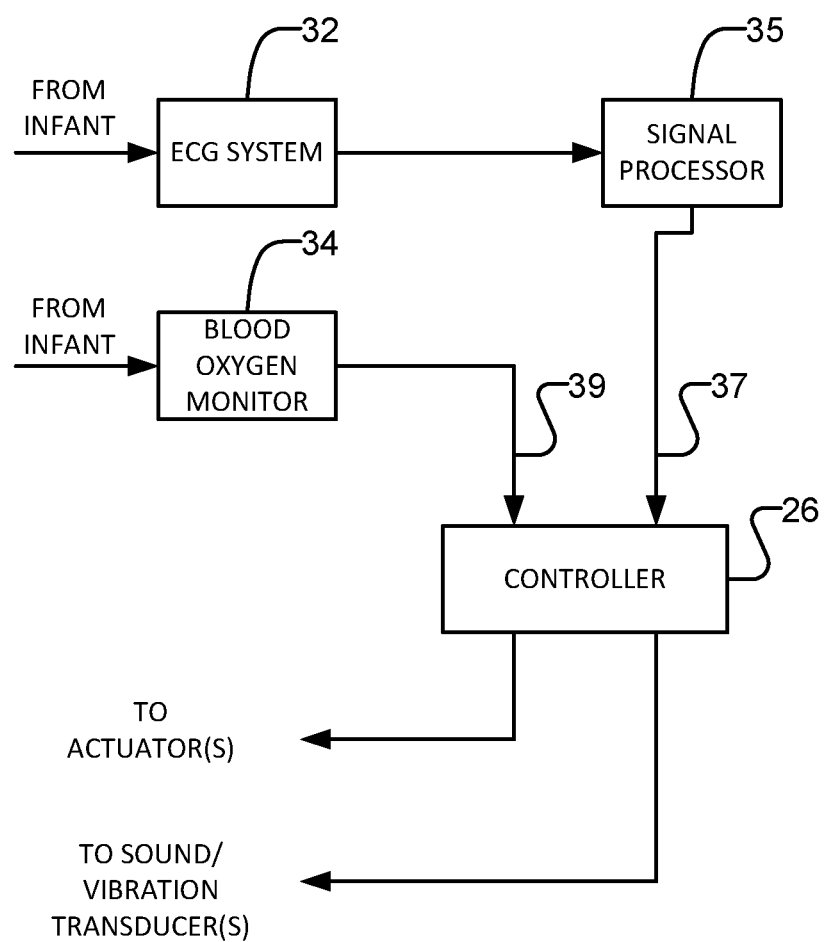
FIG. 4 is a block diagram of a control system according to an example embodiment comprising an ECG system and a blood oxygen monitor.

Stimulation as described herein is optionally controlled based at least in part on one or more of: a measure of stress in an infant (e.g. a HRV reading) and a measure of blood oxygen concentration, preferably a measure of brain blood oxygen concentration. For example, FIG. 4 shows a control system according to an example embodiment comprising an ECG system 32 and a blood oxygen monitor 34. An output of ECG system 32 is processed in a signal processor 35 to yield a signal 37 indicative of HRV. Signal processor 35 may, for example, comprise a filter or spectrum analyzer that generates signal 37 based on the power within a high frequency band of the HRV.

Controller 26 is connected to receive signal 37 and a signal 39 representing blood oxygen content from blood oxygen monitor 34. Controller 26 is configured to adjust the intensity of stimulation provided to the infant (e.g. to adjust one or more of the frequency of vertical oscillation of platform 20, the amplitude of oscillation of platform 20, the and/or character of intensity of simulated heart sounds delivered by speaker 24) based upon signals 37 and/or 39. The rate of the heart beat sounds and/or oscillations of platform 20 and/or the amplitude of heart beat sounds and/or oscillations of platform 20 may be altered within a range of set parameters which set "safe" variability. Controller 26 may then increase or decrease rates in real time according to the infant's needs. For example if HRV indicates increasing stress or brain blood oxygenation is decreasing below a threshold value or at above a threshold rate then the intensity of stimulation (frequency and/or amplitude) may be increased. Conversely, if the infant's HRV values indicate relatively low stress and satisfactory brain blood oxygen content then the intensity of stimulation may automatically be decreased. Controller 26 may optionally trigger warning or alarm signals to caregivers in an NICU, based on HRV stress or blood oxygen measurements.

In some embodiments controller 26 comprises a timer and is configured to apply stimulation in a manner coordinated with a schedule for blood tests or other pain events. For example, controller 26 may be configured to actuate activation of platform 20 a predetermined time prior to a scheduled blood test and to continue the activation of platform oscillation for a predetermined time after the scheduled blood test.

Apparatus as described herein may be applied to transport incubators as well as NICU incubators. Apparatus as described herein may be incorporated into a transport incubator. The opportunity to access advanced medical care as soon as possible after birth has a direct impact on mortality and morbidity of premature infants. The hour immediately after birth of a premature infant may be considered a 'golden hour' since effective treatment provided in that hour can markedly improve prospects for the premature infant, much in the same way that prompt treatment of traumatic injuries in adults can lead to markedly better prospects for recovery.

A transport incubator allows safe transportation of premature infants from outlying hospitals or clinics to urban medical centers in emergency situations. A transport incubator has some specific technological requirements and qualities that differ from incubators used in the NICU. These key requirements/qualities may include some or all of the following:

- Sturdier construction, capable of withstanding loads associated with transport in ambulance, helicopter, aircraft or marine rescue vessel
- A self-contained, weather proof, independent power source to provide power to life support and monitoring equipment.
- Smaller size and lighter weight, suitable for carrying by two emergency medical technicians A suspension system that reduces vibration related to motion (i.e., in airplanes, ambulances and helicopters).

An embedded life support and monitoring, comprising, for example a ventilator, intravenous pumps, and oxygen delivery systems.

Protection from environmental noise.

Features of the various embodiments described herein may be mixed and matched in any combinations or subcombinations to provide additional embodiments. The embodiments described above are merely examples which demonstrate applications of the present technology. New embodiments may be created, for example, by adding to any of the above-described embodiment one or more features from one or more other described embodiments. Other new embodiments may be created, for example, by replacing one or more features of one described embodiment with one or more features of other embodiments.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

"Premature infant incubator" means an incubator suitable for use as an incubator in a NICU or as a transportation incubator for a very or extremely premature infant. A premature infant incubator generally has a system for maintaining temperature and humidity within desired ranges.

Controllers in embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while steps are at times shown as being performed sequentially, they may instead be performed simultaneously or in different sequences. It is therefore intended that the following claims are interpreted to include all such variations as are within their intended scope.

Some aspects of the invention may also be provided in the form of a program product. The program product may comprise any non-transitory medium which carries a set of computer-readable instructions which, when executed by a data processor in a control system for apparatus as described herein cause the data processor to control the apparatus to execute a method of the invention. For example, the data processor may control an actuation system to cause a platform in an incubator to move as described in any embodiment herein and/or to cause a sound/vibration transducer to deliver stimuli to an infant as described in any embodiment herein. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. Apparatus for treating preterm infants, the apparatus comprising:
    an incubator housing;
    a warming system comprising a temperature controller connected to the incubator housing to control a temperature within the incubator housing;
    a humidifier connected to the incubator housing to maintain a desired humidity level within the incubator housing;
    a platform within the housing, the platform dimensioned to support an infant and one or more actuators connected to the platform and operable to move the platform in at least a vertical direction with an oscillating motion;
    a controller connected to the one or more actuators to control the one or more actuators to move the platform to oscillate in the vertical direction at a frequency in a range of 5 to 25 oscillations per minute;
    wherein the controller comprises a stored schedule comprising a plurality of pain events, each of the plurality of pain events associated with a time, and the controller is configured to, for each pain event of the plurality of pain events, oscillate the platform for a period commencing prior to or at the time associated with each pain event and ending after the time associated with each pain event.

2. Apparatus according to claim 1 comprising a blood oxygen sensor connected to the controller to supply a blood-oxygen signal representing blood oxygen content to the controller wherein the controller is configured to adjust one or both of the frequency and an amplitude of oscillation of the platform based on the blood-oxygen signal.

3. Apparatus according to claim 2, wherein the controller is configured to control the one or more actuators to oscillate the platform for a length of time following each pain event in the stored schedule of a plurality of pain events, wherein the length of time is at least in part based on the blood-oxygen signal.

4. Apparatus according to claim 1 comprising a heart monitor associated with a signal processor configured to process an output signal of the heart monitor signal to yield a HRV signal indicative of heart rate variability wherein the controller is configured to adjust one or both of the frequency and an amplitude of oscillation of the platform based on the HRV signal.

5. Apparatus according to claim 4 wherein the heart monitor comprises an ECG system.

6. Apparatus according to claim 4, wherein the controller is configured to control the one or more actuators to oscillate the platform for a length of time following each pain event in the stored schedule of a plurality of pain events, wherein the length of time is at least in part based on the HRV signal.

7. Apparatus according to claim 1 wherein the controller is configured to commence controlling the one or more actuators to oscillate the platform a predetermined time in advance of each pain event in the stored schedule of a plurality of pain events.

8. Apparatus according to claim 1 wherein the controller is configured to control the one or more actuators to oscillate the platform for a length of time following each pain event in the stored schedule of a plurality of pain events.

9. Apparatus according to claim 1, wherein the stored schedule of a plurality of pain events comprises a schedule of times for drawing blood from the infant.

10. A method for treating a preterm infant, the method comprising:
    placing the infant on a platform;
    prior to or at the start of each of a plurality of pain events in a stored schedule of planned pain events, commencing moving the platform to oscillate substantially vertically at a frequency in a range of 5 to 25 oscillations per minute; and
    continuing vertically oscillating the platform until after each of the plurality of pain events.

11. A method according to claim 10 wherein the infant has a gestational age of not more than 32 weeks.

12. A method according to claim 10 wherein the infant has a gestational age of not more than 30 weeks.

13. A method according to claim 10 comprising monitoring a heart rate variability of the infant and automatically adjusting one or more of the frequency and an amplitude of the oscillations in response to a measure of the infant's heart rate variability determined in the monitoring.

14. A method according to claim 10 comprising monitoring a blood oxygen level of the infant and automatically adjusting one or more of the frequency and an amplitude of the oscillations in response to a measure of the infant's blood oxygen level determined in the monitoring.

15. A method for controlling pain in a preterm infant, the method comprising:
    prior to or at the start of a scheduled pain event, placing the infant on a platform and commencing moving at least the infant's head substantially vertically by reciprocating the platform at a frequency in a range of 5 to 25 oscillations per minute;
    subjecting the infant to the scheduled pain event; and
    continuing vertically oscillating the platform after the scheduled pain event at the frequency in the range of 5 to 25 oscillations per minute,
    the oscillations before and after the scheduled pain event having an amplitude sufficient to cause in the infant a reduction in stress as demonstrated by an increase in heart rate variability of the infant.

16. A method for controlling pain according to claim 15 wherein the infant has a gestational age of 32 weeks or less.

17. A method for controlling pain according to claim 15 wherein the infant has a gestational age of 30 weeks or less.

18. A method for reducing sub-baseline fluctuations of brain blood oxygen concentration in a preterm infant, the method comprising:
    prior to or at the start of a scheduled pain event, placing the infant on a platform and commencing moving at least the infant's head substantially vertically by reciprocating the platform at a frequency in a range of 5 to 25 oscillations per minute;

subjecting the infant to the scheduled pain event; and continuing vertically oscillating the platform after the scheduled pain event at the frequency in the range of 5 to 25 oscillations per minute, the oscillations before and after the scheduled pain event having an amplitude sufficient to cause in the infant a reduction in sub-baseline fluctuations of brain blood oxygen concentration as demonstrated by non-invasive transcranial NIRS measurements of the blood oxygen concentration in the infant's brain.

19. A method for reducing sub-baseline fluctuations of brain blood oxygen concentration according to claim 18 wherein the infant has a gestational age of 32 weeks or less.

20. A method for reducing sub-baseline fluctuations of brain blood oxygen concentration according to claim 18 wherein the infant has a gestational age of 30 weeks or less.

21. A method as defined in claim 18 comprising providing the oscillation continuously for a period of hours.

* * * * *